(12) United States Patent
Terao

(10) Patent No.: US 8,974,480 B2
(45) Date of Patent: *Mar. 10, 2015

(54) NUCLEUS CHOPPER AND SPLITTER

(75) Inventor: Kenichi Terao, Tokyo (JP)

(73) Assignee: Asico, LLC., Westmont, IL (US)

( * ) Notice: Subject to any disclaimer, the term of this patent is extended or adjusted under 35 U.S.C. 154(b) by 267 days.

This patent is subject to a terminal disclaimer.

(21) Appl. No.: 13/570,654

(22) Filed: Aug. 9, 2012

(65) Prior Publication Data

US 2013/0204283 A1 Aug. 8, 2013

Related U.S. Application Data

(62) Division of application No. 11/069,774, filed on Mar. 1, 2005, now Pat. No. 8,262,682.

(60) Provisional application No. 60/600,673, filed on Aug. 10, 2004.

(51) Int. Cl.
*A61B 17/32* (2006.01)
*A61F 9/007* (2006.01)
*A61B 17/3211* (2006.01)
*A61B 17/30* (2006.01)

(52) U.S. Cl.
CPC ......... *A61F 9/00736* (2013.01); *A61B 17/3211* (2013.01); *A61F 9/00754* (2013.01); *A61B 17/30* (2013.01); *A61B 2017/305* (2013.01)
USPC ....................................................... 606/170

(58) Field of Classification Search
USPC .................................. 606/166, 167, 170, 174
See application file for complete search history.

(56) References Cited

U.S. PATENT DOCUMENTS

| | | | | | |
|---|---|---|---|---|---|
| 4,497,320 | A | * | 2/1985 | Nicholson et al. | 606/79 |
| 5,167,618 | A | * | 12/1992 | Kershner | 604/22 |
| 5,281,230 | A | * | 1/1994 | Heidmueller | 606/127 |
| 5,290,302 | A | * | 3/1994 | Pericic | 606/167 |
| 5,308,357 | A | * | 5/1994 | Lichtman | 606/205 |
| 5,370,658 | A | * | 12/1994 | Scheller et al. | 606/205 |
| 5,383,877 | A | * | 1/1995 | Clarke | 606/148 |
| 5,400,768 | A | * | 3/1995 | McNamara et al. | 600/104 |
| 5,501,698 | A | * | 3/1996 | Roth et al. | 606/205 |
| 5,749,886 | A | * | 5/1998 | Abidin et al. | 606/182 |
| 5,893,873 | A | * | 4/1999 | Rader et al. | 606/205 |
| 5,893,877 | A | * | 4/1999 | Gampp et al. | 606/205 |
| 6,051,004 | A | * | 4/2000 | Gill | 606/147 |
| 6,306,155 | B1 | * | 10/2001 | Chandler et al. | 606/205 |
| 6,855,156 | B2 | * | 2/2005 | Etter et al. | 606/205 |
| 6,908,476 | B2 | * | 6/2005 | Jud et al. | 606/205 |
| 7,011,666 | B2 | * | 3/2006 | Feinsod | 606/107 |
| 8,262,682 | B2 | * | 9/2012 | Terao | 606/170 |
| 2001/0056286 | A1 | * | 12/2001 | Etter et al. | 606/205 |
| 2002/0062131 | A1 | * | 5/2002 | Gallo, Sr. | 606/167 |
| 2003/0093099 | A1 | * | 5/2003 | Anthone | 606/166 |
| 2003/0120305 | A1 | * | 6/2003 | Jud et al. | 606/205 |
| 2006/0036270 | A1 | * | 2/2006 | Terao | 606/167 |
| 2013/0204283 | A1 | * | 8/2013 | Terao | 606/167 |
| 2013/0211414 | A1 | * | 8/2013 | Terao | 606/107 |

* cited by examiner

*Primary Examiner* — Ryan Severson
(74) *Attorney, Agent, or Firm* — Wood, Phillips, Katz, Clark & Mortimer

(57) ABSTRACT

A surgical instrument which both incises and splits the nucleus of a lens has a pair of 5 spring steel segments slidably received in a metallic tube. Each segment terminates in a tip. As the spring steel segments are drawn into the tube the tips come together to form a cutting edge useful for incising the lens. When the segments are extended from the tube the tips separate, forcing the incision open until the lens is split.

10 Claims, 8 Drawing Sheets

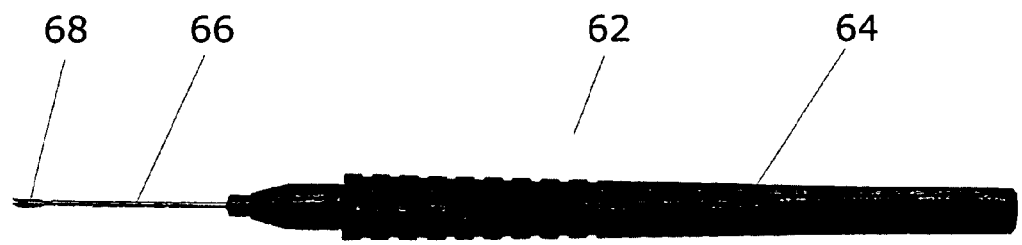
Fig. 6        Prior Art
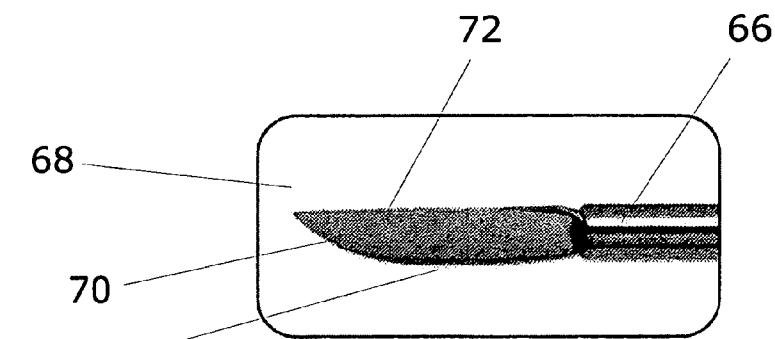
Fig. 7    Prior Art
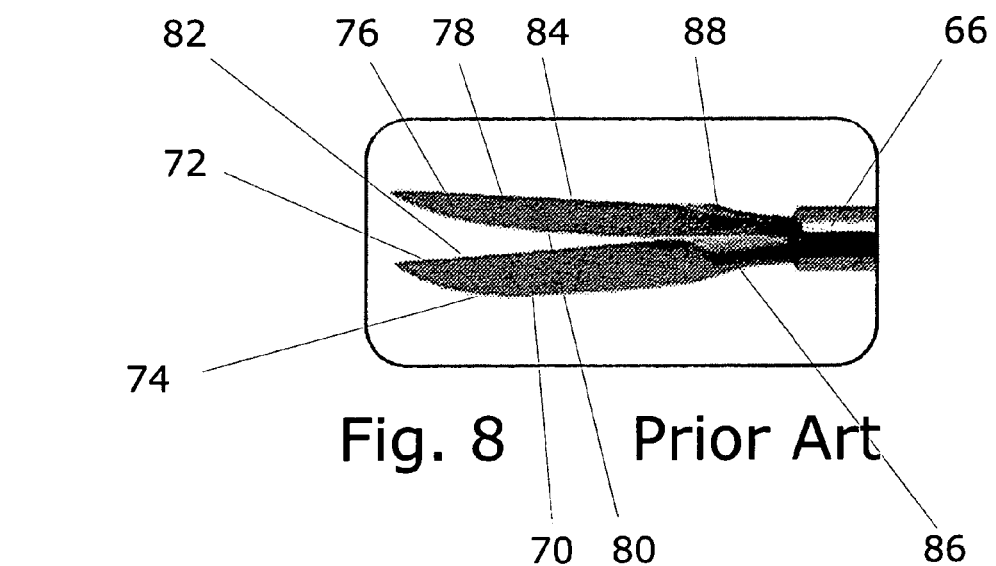
Fig. 8       Prior Art

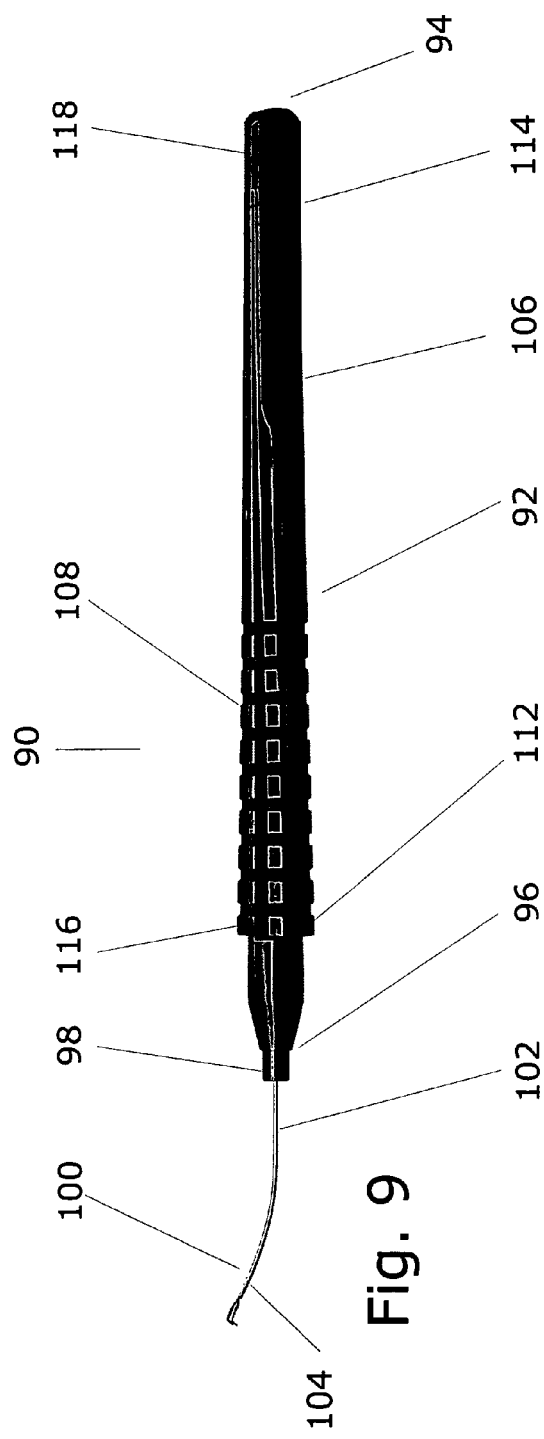
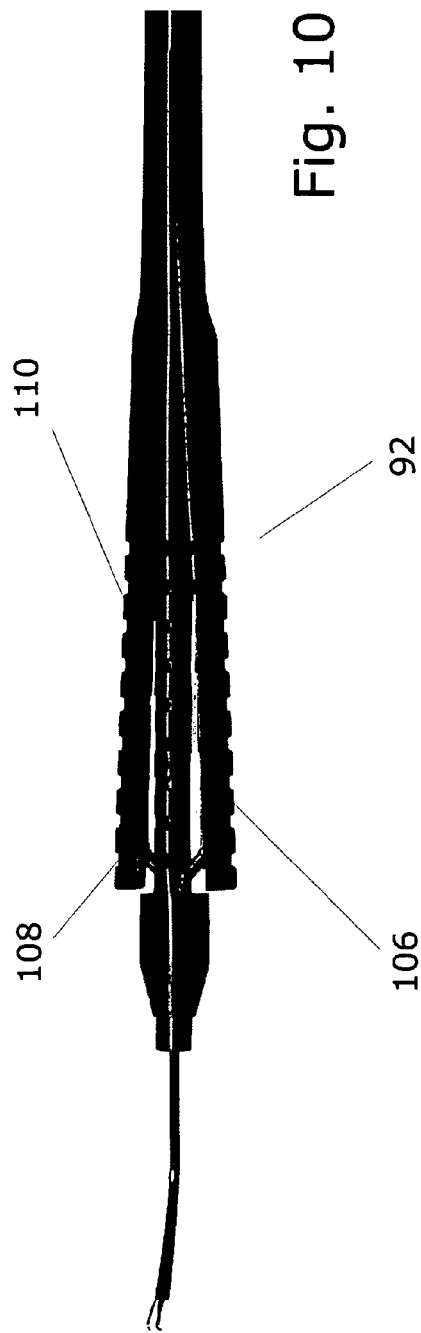

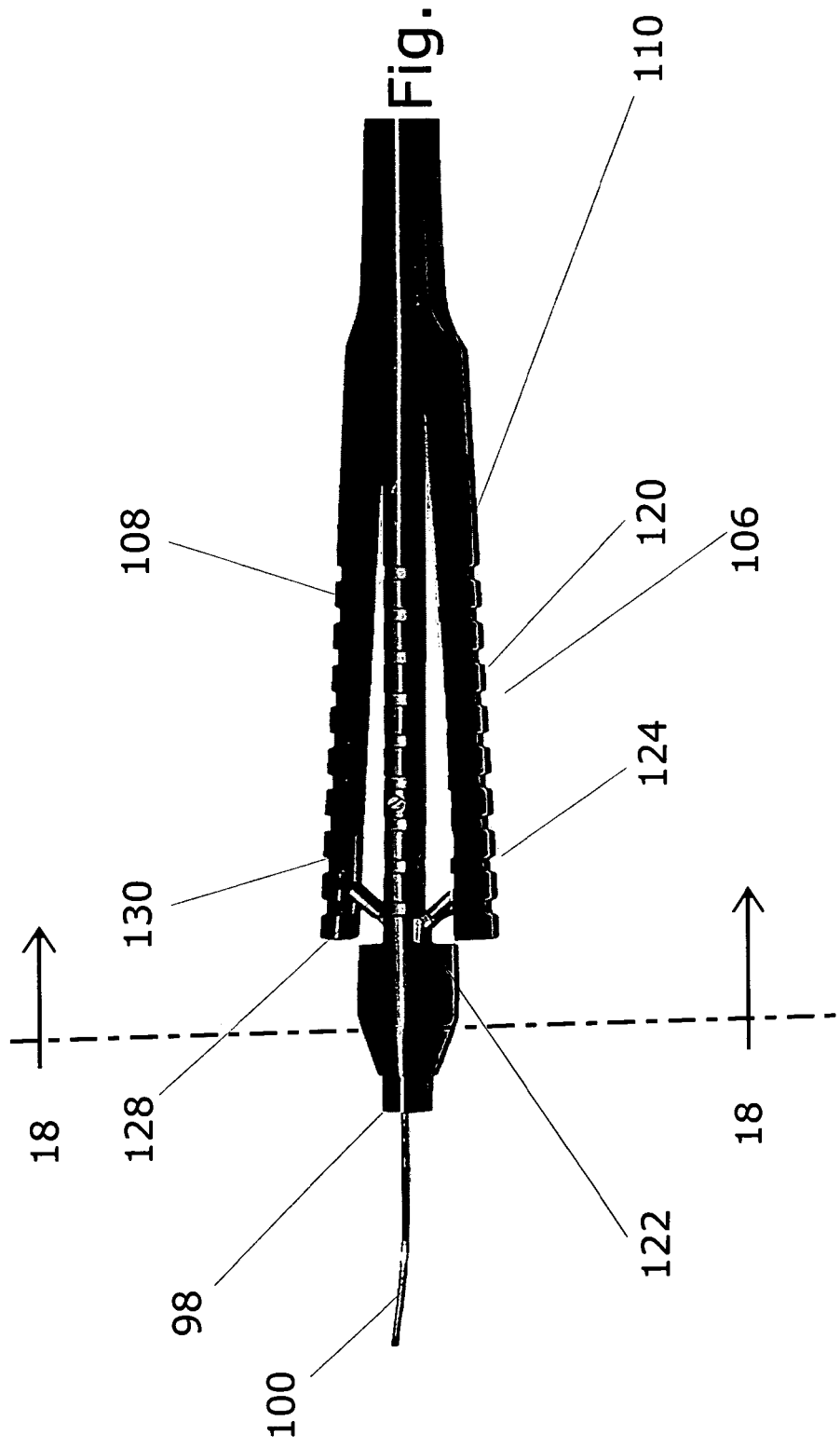

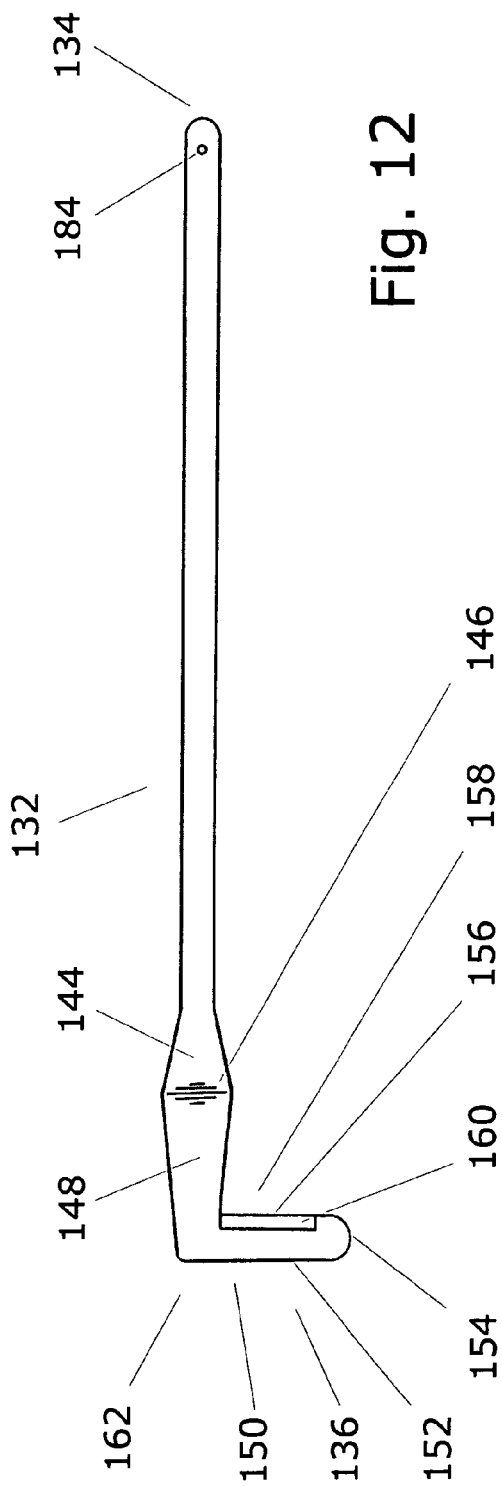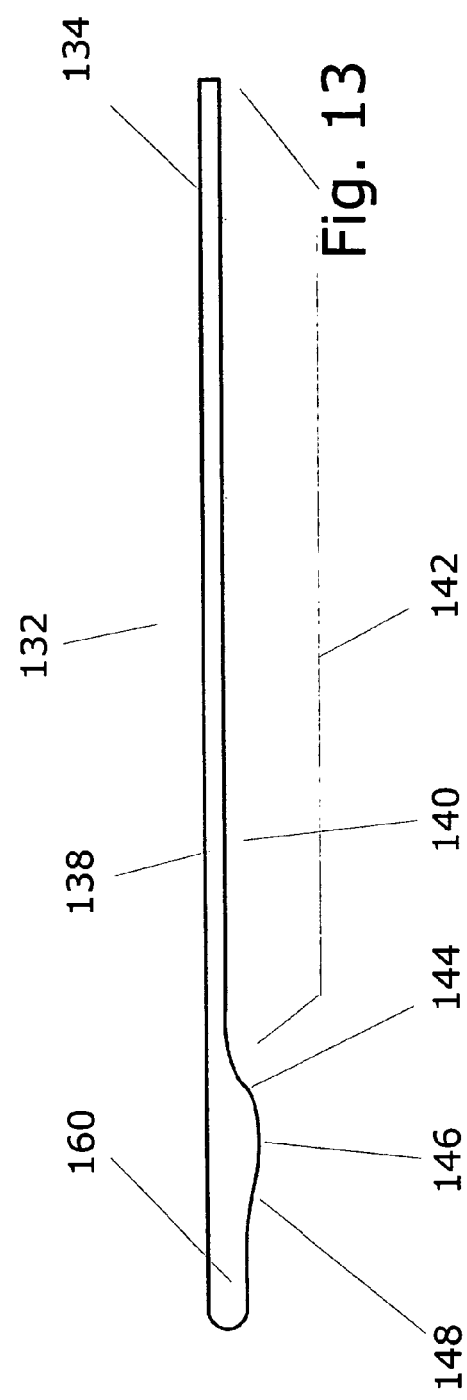

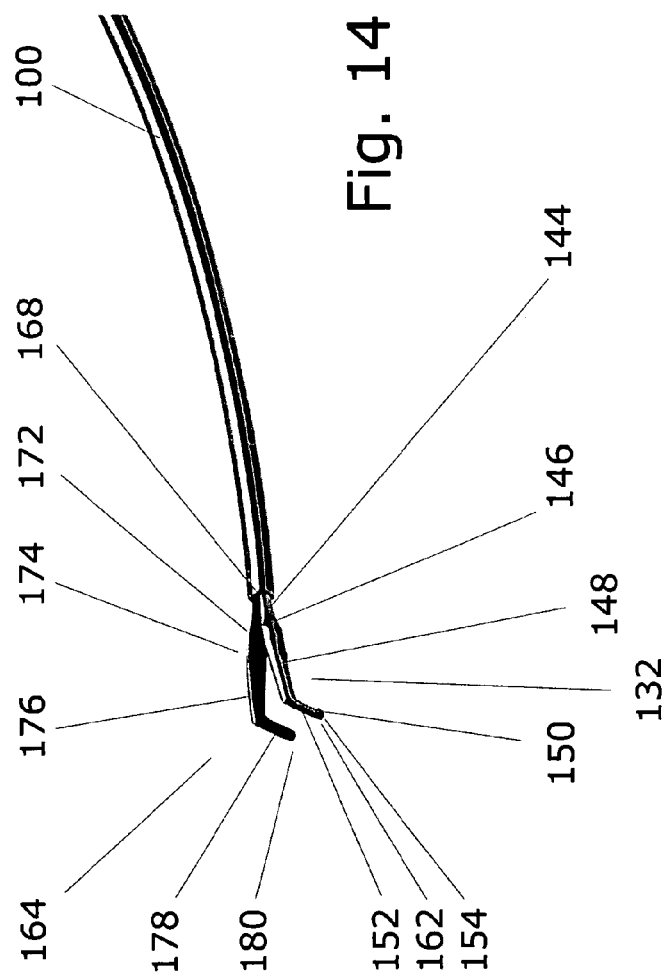
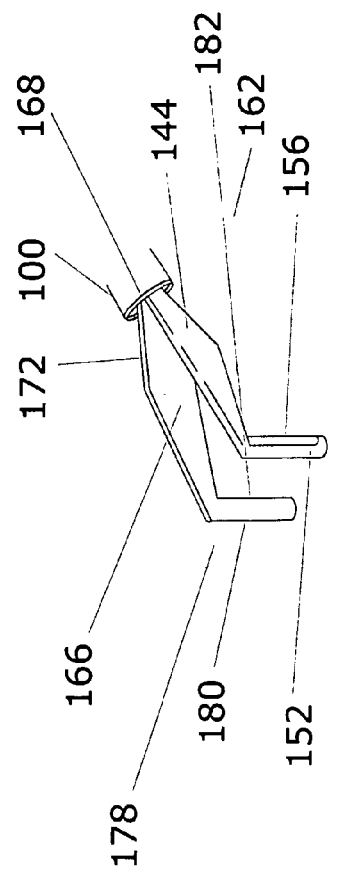

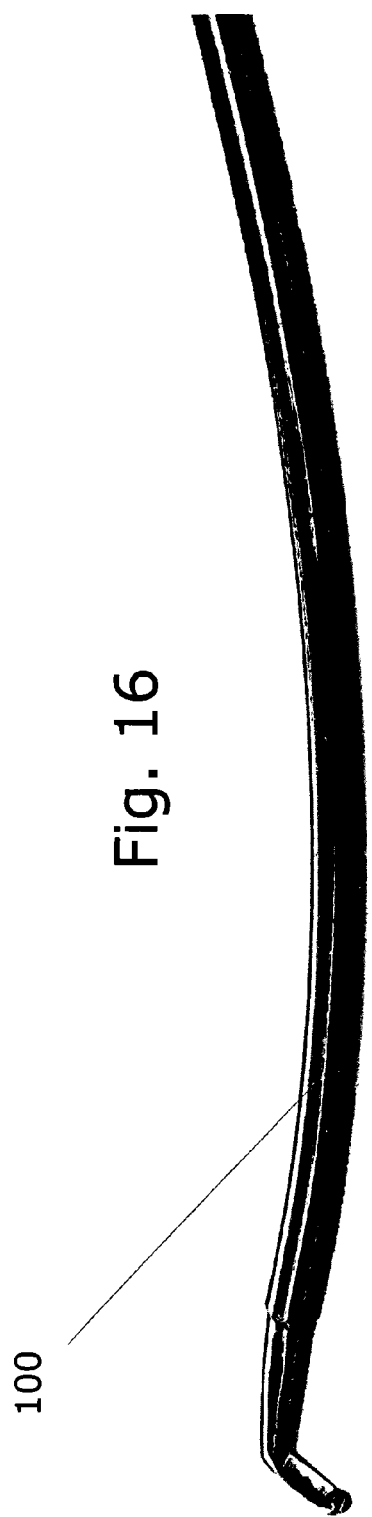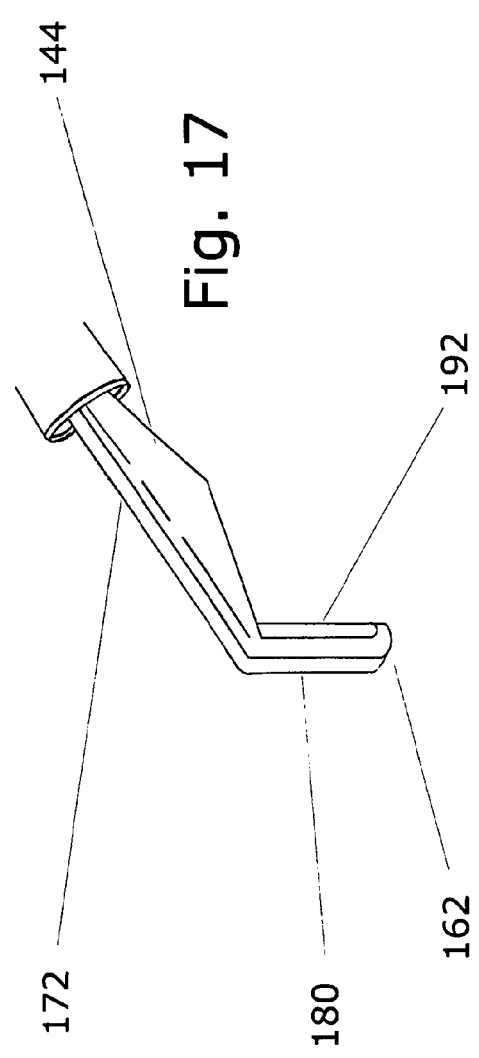

NUCLEUS CHOPPER AND SPLITTER

This is a division of application Ser. No. 11/069,774, filed 1 Mar. 2005 and entitled "Combined Chopper and Splitter" which claims priority from application Ser. No. 60/600,673, filed 10 Aug. 2004 and entitled "Combined Chopper and Splitter", both of which are hereby fully incorporated herein by reference.

FIELD OF THE INVENTION

The present invention relates generally to surgical instruments used in opthalmological surgery and, more particularly, to an instrument which can perform both chopping and splitting operations as part of cataract removal.

BACKGROUND OF THE INVENTION

Phacoemulsification has come to be a technique of choice for the removal of damaged or diseased lenses from the eye. Commonly, such surgery is called for when a patient develops cataracts, a condition in which a portion of the eye lens becomes hard and opaque. Unless the damaged lens is removed and replaced with a properly selected artificial lens, blindness or severely impaired vision will result.

Phacoemulsification is the use of ultrasonic energy to emulsify the damaged lens and aspirate the resulting lens particles from the eye. One of the most significant advantages of the use of phacoemulsification is that the apparatus itself is small and can fit through a relatively small incision, resulting in less fluid leakage from the eye capsule and shorter patient recovery times. It is desirable to limit the amount of ultrasonic energy used as much as possible in order to minimize the risk of damage to eye tissue. Often, the lens nucleus (the hardest portion of the lens) is chopped or split into smaller pieces prior to or during phacoemulsification. Smaller pieces require less energy to emulsify, and this shortens the time during which ultrasonic energy is actually being supplied to the phacoemulsification apparatus.

Known fractionating techniques include making incisions into the lens and, thereafter, prying the incisions open to split the lens into halves or quarters. As an example, U.S. Pat. No. 5,147,368 (Brown) teaches and describes a nucleus splitter in the form of a forceps, the jaws of which are intended to be inserted into a groove or incision already cut in the nucleus. When the handle of the nucleus splitter is squeezed, the jaws are forced apart thereby prying apart the groove or incision or splitting or cracking the nucleus into fragments.

U.S. Pat. No. 4,428,748 (Peyman, et al.) teaches and describes a combined ultrasonic emulsifier and mechanical cutter for surgery. This device includes the typical components of a phacoemulsification apparatus, namely, an ultrasonically vibrated hollow needle and one or more aspiration ports through which the emulsified lens particles are drawn and evacuated from the eye capsule. Peyman, et al. also includes a rotary mechanical cutter formed in the tip of the apparatus to be used for cutting nuclear tissue.

U.S. Pat. No. 6,592,541 (Kurwa) teaches and describes an opthamological surgical instrument device and method of use in which the tip of a phacoemulsification needle is formed with a cutting edge which can be inserted into the nucleus for the purpose of making an incision. As described by the inventor, a nucleus cracker or pre-chopper is then required to split the nucleus after which the phacoemulsification instrument is reinserted and used to emulsify and aspirate the lens fragments.

As used throughout, the term "pre-chopping" refers to the opthalmological surgical technique of making a plunge cut directly downward into the nucleus in order to form a channel or incision. The term "chopping" refers to the technique of forming grooves or incisions in the eye by drawing an instrument having a cutting edge across the lens.

Examples of known prior art choppers are illustrated in the accompanying drawings. One such chopper identified as Model No. AE-2515 sold by ASICO LLC of Westmont, Ill. is shown in FIGS. 1, 2 and 3 and consists of an elongated shaft having a blade portion formed at the end of the shaft and extending at an angle to the shaft. The cutting edge of the blade portion faces toward the handle of the instrument, meaning an incision is made when the instrument is placed on the nucleus and then drawn across the nucleus. This instrument is available in both 90 degree and 60 degree angled cutting edges.

Another prior art chopper is identified as Model No. AE-2523 manufactured by ASICO LLC and consists of an elongated shaft with a hook-like projection extending at an angle to the shaft. As with the Model AE-2515, a cutting edge is formed on the interior surface of the hook and cutting occurs when the chopper is drawn across the nucleus. The hook shape allows the Model AE-2523 to be used to manipulate the lens within the capsule. Thus, once a first incision is made, the lens may be rotated 90 degrees and a second incision made to divide the lens into four quadrants.

FIGS. 6, 7 and 8 show a prior art pre-chopper identified as Model No. AE-4287, sold by ASICO LLC. As described in more detailed herein, the Model AE-4287 has a spring steel blade assembly positioned within a tube with the end of the blade assembly forming a pair of blade leaves. The handle of the instrument is manufactured with a linkage which, in its normal position, is spread apart, a position in which the blade leaves are separated. When the handle is squeezed, the blade assembly is drawn into the blade tube and the two leaves are forced together to form a single solid blade. This blade has an upper straight surface which is sharpened and a lower curved surface which is blunt. In use, the AE4287 pre-chopper is inserted into the eye capsule and is rotated to bring the straight sharpened edge into contact with the upper surface of the lens. A plunge cut is then made to form a partial incision. The instrument is then turned 180 degrees to bring the blunt portion of the blade assembly into contact with the lens, within the incision. Thereafter, when the handle linkage is released, the leaves separate exerting a splitting or cracking force on the lens along the incision made by the pre-chopper. After several such incisions are made, and the lens is fractionated, the lens fractions may be emulsified and removed by phacoemulsification.

BRIEF DESCRIPTION OF THE INVENTION

The present invention is a surgical instrument which both incises and splits the nucleus of a lens in a manner which does not require the use of a pre-chopper.

Pursuant to the present invention, and in accordance with the teachings of the pre-chopper described above, a pair of spring steel segments are inserted into a metallic tube and may be drawn inwardly and outwardly along the tube axis. Along most of its length, each spring steel segment has a constant cross sectional dimension and is identical in dimension to the mating spring steel segment. For the purposes of this description, the spring steel segment's assembly will be referred to as a having a left hand and a right hand segment which are mirror images of each other. Each segment has an inner and an outer surface and, when assembled, the inner surfaces abut one another.

At the distal end of each spring steel segment a tip is formed. The tip consists of a first, ramped section formed on the outer surface and extending generally axially with the tube axis, and a second depending segment having a blunt leading edge and a sharpened trailing edge. Each depending segment terminates in a rounded, blunt end.

As the spring steel segments are drawn inward axially into the tube, the ramp portions on the outer surfaces contact the inner surface of the tube and the tips are pressed tightly together to form a single, virtually solid cutting blade. The blade may then be placed at one edge of the lens and drawn across the lens to form an incision.

The present invention also includes a handle with a spring biased linkage which, when unstressed, allows the spring steel segments to extend from the tube, leaving the left and right tips separated. When the handle of the instrument is squeezed the linkage acts to pull the spring steel segments into the tube thereby forcing the tips together to form the single, virtually solid cutting blade.

In use, after an incision has been made, the tip is placed in the incision and the pressure on the handle is released, allowing the blades to separate and exert a separating or cracking force along the length of the incision. Where required the first incision is deepened by subsequent additional passes of the tip until the incision is deep enough to allow the lens to be split by allowing the blade segments to separate. These steps can be repeated until the lens is successfully fractionated.

The size and shape of the blade ends is such that a relatively small incision along the order of 0.8 mm can be used to allow access to the lens.

While the following describes a preferred embodiment or embodiments of the present invention, it is to be understood that this description is made by way of example only and is not intended to limit the scope of the present invention. It is expected that alterations and further modifications, as well as other and further applications of the principles of the present invention will occur to others skilled in the art to which the invention relates and, while differing from the foregoing, remain within the spirit and scope of the invention as herein described and claimed. Where means-plus-function clauses are used in the claims such language is intended to cover the structures described herein as performing the recited functions and not only structural equivalents but equivalent structures as well. For the purposes of the present disclosure, two structures that perform the same function within an environment described above may be equivalent structures.

BRIEF DESCRIPTION OF THE DRAWINGS

The foregoing will become more apparent upon consideration of the accompanying drawing figures in which:

FIG. 6 is a perspective view of a prior art pre-chopper, ASICO Model AE-4287;

FIG. 7 is an enlarged view of the blade leaves of the pre-chopper shown in FIG. 6 shown in the closed position;

FIG. 8 is an enlarged view of the blade leaves of the pre-chopper shown in FIG. 6 shown in the separated position;

FIG. 9 is a perspective view of a preferred embodiment of the present invention;

FIG. 10 is an enlarged view of a portion of the instrument shown in FIG. 9 showing the handle linkage in its open position;

FIG. 11 is an enlarged view of a portion of the view of FIG. 10 showing the linkage in greater detail;

FIG. 12 is a lateral schematic view of a left blade segment;

FIG. 13 is a top schematic view of the blade segment of FIG. 12;

FIG. 14 is an enlarged view of the blade leaves extending from the blade tube shown in the open position;

FIG. 15 is an enlarged detail of the blades shown in the open position;

FIG. 16 is an enlarged perspective view of the blade leaves extending from the blade tube and shown in the closed position;

FIG. 17 is an enlarged detail of the blade leaves shown in the closed position.

DETAILED DESCRIPTION OF THE DRAWINGS

Figure 1:
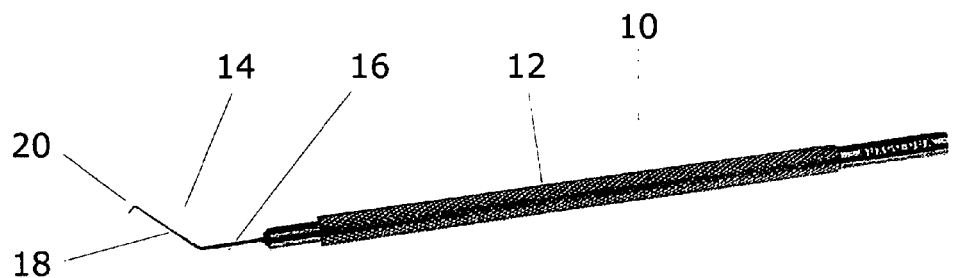
FIG. 1 is a perspective view of a first prior art chopper, ASICO Model AE-2515.

Referring now to FIG. 1, the numeral 10 indicates generally a first prior art chopper having a solid metallic body 12 from which a chopper blade 14 extends. As seen in FIG. 1, blade 14 has a first segment 16 generally coaxial with handle 12 a second segment 18 angled with respect to first segment 16 and a blade tip 20.

Figure 2:
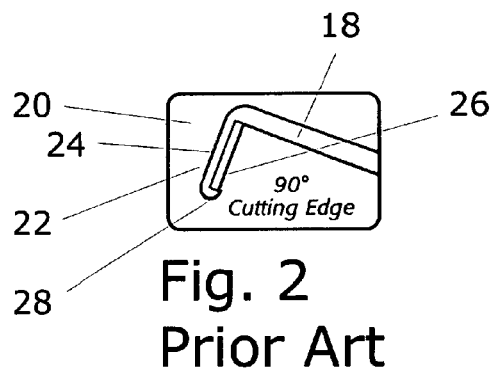
FIG. 2 is an enlarged view of the blade end of the chopper of FIG. 1 showing the blade with a 90 degree cutting edge.

Referring now to FIG. 2, blade tip 20 is shown in an enlarged view as having a depending blade segment 22 extending at generally right angles to second blade segment 18. Blade segment 22 has a lead surface 24 which is polished and rounded in shape and a trailing surface 26 formed as a cutting edge. Cutting edge 26 terminates in a rounded bottom 28, formed as a smooth surface to protect other tissue in the eye.

Figure 3:
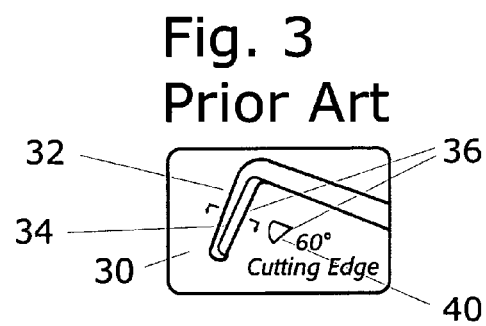
FIG. 3 is an enlarged view of the blade end of FIG. 1 showing the blade with a 60 degree cutting edge.

Referring now to FIG. 3, a second tip embodiment 30 is shown having a lead or distal edge 32 which is formed with a rounded and smoothed surface 34. Opposite surface 34, a cutting edge 36 is formed and the small sectional view shown in FIG. 3 demonstrates that cutting edge 36 is formed by the intersection of surfaces 38 and 40 at a 60° angle.

Figure 4:
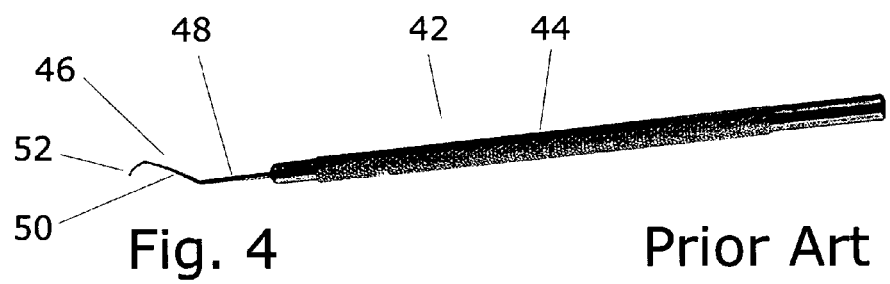
FIG. 4 is a perspective view of a second prior art chopper, ASICO Model AE-2523.
Figure 5:
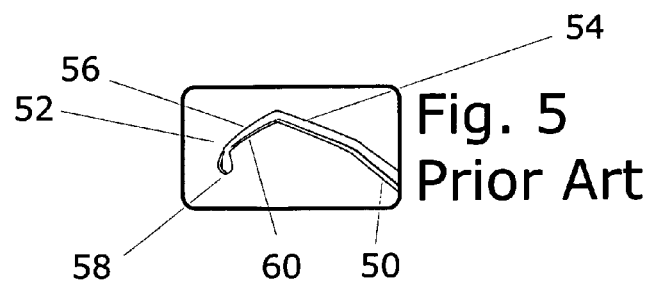
FIG. 5 is an enlarged view of the blade end of the chopper shown in FIG. 4.

Referring now to FIG. 4, a second prior art chopper 42 is shown, identified as ASICO Model AE-2523. Chopper 42 has a solid metallic handle 44 with a blade 46 extending therefrom. Blade 46 has a first segment 48 coaxial with handle 44, a second segment 50 extending at an angle to first segment 48 and a hook segment 52 which forms the terminus of segment 50. As seen in FIG. 5, hook segment 52 has a first hook segment 54 angled with respect to segment 50, a second hook segment 56 and a terminus 58. Terminus 58 is rounded and smoothed to protect any eye tissue with which it may come into contact from being cut. The trailing surface of second hook segment 56 has a cutting edge 60 formed thereon which performs the cutting or incising operation when chopper 42 is drawn across an eye lens.

Referring now to FIG. 6, the numeral 62 refers generally to a prior art pre-chopper identified above as ASICO Model AE-4287. Pre-chopper 62 has a handle assembly 64 to which is affixed a guide tube 66 from which protrudes a pre-chopper blade assembly 68. Blade assembly 68, while not shown herein in detail, comprises a pair of blade segments formed from spring steel which have a natural tendency to curl away from each other.

Referring now to FIG. 7, an enlarged view of pre-chopper blade assembly 68 is shown. Left hand leaf 70 is shown having an upper cutting edge 72 and a lower blunt edge 74 formed thereon. In this embodiment, sharp edge 72 is formed as a straight edge while blunt edge 74 is formed as a curved edge.

Referring now to FIG. 8, left blade leaf 70 is shown paired with right leaf 76. As with left leaf 74, right leaf 76 has an upper, sharpened surface 78 and a lower blunt surface 80. It should be understood that left leaf 70 and right leaf 76 are mirror images of each other and that the interior surface 82 of left leaf 70 is flat as is the interior surface of right leaf 84.

Also as seen in FIG. 8, left leaf 70 has a blade ramp 86 formed thereon and right blade leaf 76 has a mirror image ramp 88 formed thereon.

When handle 64 of pre-chopper 62 is unstressed, the left and right leaves 70, 76 are positioned apart as shown in FIG. 8. When handle 64 is squeezed, guide tube 66 is moved axially forward. When ramps 86, 88 come into contact with the interior surface of tube 66, leaves 70, 76 are forced inward towards each other until they abut as shown in FIG. 7. In this position, edges 72, 78 act as a single cutting edge while lower surfaces 74, 80 act as a single blunt surface.

Referring now to FIG. 9, the numeral 90 refers generally to an instrument for chopping and splitting lenses incorporating a preferred embodiment of the invention. Instrument 90 has a handle 92 with a distal end 94 and a proximal end 96. A mounting hub 98 is attached to handle 90 at proximal end 96. A guide tube 100 is slidable received through a central channel formed in hub 98, shown in greater detail below. As shown in the embodiment of FIG. 9, guide tube 100 has a first, rectilinear segment 102 extending from hub 98 and a second curved segment 104 integral with segment 102.

Referring now to FIG. 10 handle 92 is shown having a left handle grip 106 and a right handle grip 108. Handle 92 also includes a central handle plate 110. As seen in FIG. 9, left handle grip 110 has a proximal end 112 and a distal end 114. Left handle grip 106 is attached to central handle plate 110 at distal end 114.

In like fashion, right handle grip 108 has a proximal end 116 and a distal end 118, and is attached to central handle plate 110 at distal end 118.

Preferably, left and right handle grips 106, 108 are formed from spring steel segments or segments having a natural spring such that when distal ends 114, 118 are attached to central handle plate 110, left and right handle grips 106, 108 bend away and are spaced apart from central handle plate 110. In other words, proximal ends 112, 116 when not gripped extend apart and away from central handle plate 110.

Referring now to FIG. 11, central handle plate 110 has a slider plate channel 120 formed therethrough proximate nib 98. A slider plate 122 is inserted into plate channel 120 and slides axially along channel 120 between the forwardmost and rearmost ends of channel 120. For the purposes of this description, the direction axially toward tube 100 will be referred to as the forward axial direction and movement axially toward distal end 94 will be referred to as the rearward direction.

As seen in FIG. 11, a left handle link 124 has two ends, one of which is pivotally attached to slider plate 122. The remaining end of left handle link 124 is slidably secured to left handle grip 106 as described below.

A right handle link 128 having two ends is pivotally secured at one end to slider plate 122 in the same manner as left handle link 124.

Right handle grip 108 has a right handle slider groove 130 formed therein, proximate end 116. As seen in FIG. 11, right handle line 128 is slidably secured at its other end within right hand slider groove 130. In identical fashion, left handle link 124 is secured within identical formed groove 126 (not shown) formed in left handle grip 106 proximate proximal end 112. Links 124, 128 are mechanically attached such that when left and right handle grips 106, 108 are gripped and moved toward central handle plate 110, slider plate 122 moves in an axially forward direction.

Referring now to FIG. 12, a schematic lateral elevation of a blade segment 132 is shown. Segment 132 is preferably formed from flat spring type surgical stainless steel. In this preferred embodiment, blade segment 132 has a distal end 134 and a proximal end 136. FIG. 13 is a top view of the blade segment 132 of FIG. 12. As seen, blade segment 132 has an interior surface 138 and an exterior surface 140. Interior surface 138 is formed as a flat surface throughout. External surface 140 is formed with a first flat segment 142 integrally formed with a ramp segment 144 which is progressively thicker in dimension than segment 142 until it reaches a maximum thickness at break 146. Thereafter, surface 140 tapers along segment 148 to proximal end 136.

Referring again to FIG. 12, distal end 136 is shown having a depending blade 150, depending from segment 148 at approximately a 90 degree angle. Blade 150 has a lead surface 152 which, in this preferred embodiment, is machined to be smooth and curved.

Blade 150 terminates in a bottom 154 which is also smooth and rounded. Blade 150 has a cutting edge 156 formed along a portion of trailing surface 158. In the embodiment shown, cutting edge 156 is shown by the intersection of angled surfaces 160, 162 which, in a preferred embodiment, meet at an angle of 90 degrees.

Segments 144, 146, 148 and 150 constitute left tip 162.

In this preferred embodiment, a right blade segment 164 is formed as a mirror image of left segment 132 and has a right inner surface 166. When assembled, left and right inner surfaces 138, 166 are in face-to-face contact along their respective lengths as described hereinafter.

Referring now to FIG. 14, a portion of guide tube 66 is shown with left and right blade segments 132, 164 slidably inserted therein. As shown in FIG. 14, the entire length of segment 132 is within tube 66. Protruding from tube end 168 is tip 162, including ramp segment 144, break 146, segment 148 and blade 150 of left blade segment 132. In similar fashion, segment 164 has a corresponding ramp segment 172, a corresponding break 174, a corresponding segment 176, and a corresponding blade 178 which collectively form right tip 180. It is to be understood that a right blade segment 170 corresponding to left blade segment 142 is also inserted within tube 66 in face to face contact with left segment 142.

Referring now to FIG. 15, an enlarged view of end 168 of tube 100 is shown with left and right lead surfaces 152, 178, left cutting edge 156 and a corresponding right cutting edge 182, a portion of right inner surface 166 and left and right ramps 144, 172.

In this preferred embodiment, left and right blade segments 132, 164 are secured to handle plate 110 and are held stationary with respect to instrument 90.

Referring now to FIG. 16, a portion of guide tube 100 is shown with guide tube 100 in its extended position as left and right handle segments 106, 110 are compressed to move slider plate 122 in an axially forward position. As shown in greater detail in FIG. 17, when left and right ramps 144, 172 contact guide tube 100, as slider plate 122 is being moved forward, left tip 162 is moved toward right tip 180 until inner surfaces 138, 166 are in contact along the entire length of blade segments 132, 164. When this occurs, left and right cutting edges 156, 182 are juxtaposed along their entire lengths to form, effectively a single cutting blade 192 as shown in FIG. 17.

Figure 18:
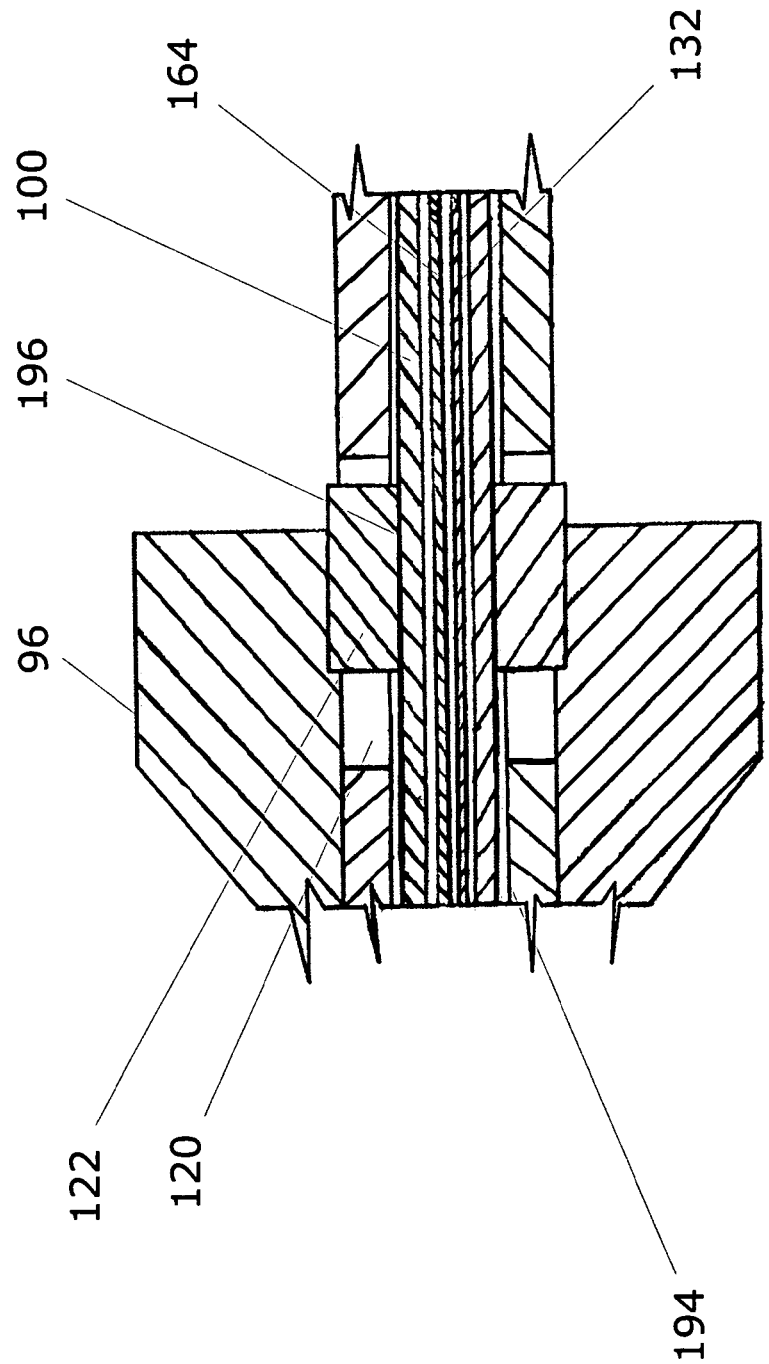
FIG. 18 is a partial sectional view taken along line 18-18 of FIG. 12.

Referring now to FIG. 18 a partial sectional schematic view of a preferred embodiment showing slider block 122 is shown. Hub 96 has a centrally positioned axial tube guide channel 194 formed therethrough. Slider block 122 has a central, axially extending tube mounting aperture 196 formed therethrough. within which guide tube 100 is received and gripped after it has been passed though aperture 194. Left and right spring steel segments 132, 164 are positioned within guide tube 100 and, because they are attached to handle plate 110 do not move when slider block 122 is moved in slot 120 to move guide tube 100 into or out of hub 96.

As seen in FIGS. 16 and 17, with left and right handle grips 106, 108, compressed, instrument 90 may be used as a chopper by positioning blade 192 at a far end of the lens and drawing it across the lens to form a groove. After the groove is formed, blade 192 is positioned within the groove and the pressure on handle grips 106, 108 is controllably released to allow blade segments 132, 164 to again extend from guide tube 100 thereby separating tips 162, 180. When this occurs, surface segments 144, 146, 148 and 150 of left segment 132 and corresponding surfaces 172, 174, 176 and 178 of right segment 164 contact side walls of the groove and force the groove to widen. In this embodiment, the actions of chopping and "cracking" are repeated until the lens has separated into distinct segments.

When blade 192 is formed, it may also be used to manipulate and maneuver the lens into a position where a second cut may be made.

Thus, the procedures of chopping and cracking are accomplished through the use of a single instrument which, when inserted into the eye capsule, need not be removed until the chopping and splitting procedures have been completed. Once completed, the phacoemulsification instrument may be inserted and the chopped segments may be emulsified and aspirated in less time, using less energy than would be possible if the lens were not to be cracked.

I claim:

1. A surgical instrument with an exposed cutting edge for cutting body tissue, said instrument comprising:
    a handle assembly, said handle assembly having a proximal end and a distal end;
    a first segment extending from said handle assembly proximal end, said first segment movable with respect to said handle assembly, said first segment having a tip and a first blade depending from said tip;
    a second segment extending from said handle assembly proximal end, said second segment movable with respect to said handle assembly, said second segment having a tip and a second blade depending from said tip;
    each of said first and second blades having a leading edge and a trailing edge, said handle assembly movable for: (i) moving said first and second blades into contact with one another; and (ii) for moving said first and second blades apart from one another; and
    said trailing edges forming a single exposed and unenclosed cutting edge when said first and second blades are moved into contact one with one another, whereby said cutting edge can be used to form a cut in said body tissue and said first and second blades can be used to widen said cut when said first and second blades are moved away from one another.

2. The surgical instrument as recited in claim 1 wherein said leading edges are substantially smooth and curved.

3. The surgical instrument as recited in claim 1 wherein said trailing edges are substantially straight.

4. The surgical instrument as recited in claim 1 wherein said surgical instrument further comprises a mounting hub positioned at said handle assembly proximal end;
    a guide tube attached to and extending from said mounting hub;
    wherein activation of said handle assembly causes at least one of said first and second segments to engage with said guide tube to move at least one of said first and second blades toward the other of said first and second blades.

5. The surgical instrument as recited in claim 4 wherein said first and second segments further comprise first and second ramps for being engaged with said guide tube to move said first and second blades together.

6. The surgical instrument as recited in claim 4 wherein said handle assembly further comprises first and second handle grips pivotally attached to said handle assembly,
    said first and second segments operatively engaged with said first and second handle grips whereby movement of said handle grips in a first direction brings said blades into contact with one another and movement of said handle grips in a second direction separates said blades from one another.

7. The surgical instrument as recited in claim 6 wherein said first and second handle grips are biased apart to take a first, uncompressed position and are moveable toward one another to a second, compressed position.

8. The surgical instrument as recited in claim 1 wherein said first and second blades are substantially identical.

9. A method for chopping and splitting the nucleus of an eye with a surgical instrument, said method comprising the steps of:
    (a) providing a surgical instrument, said surgical instrument having
        (i) a handle assembly with a proximal end and a distal end,
        (ii) a first segment extending from said handle assembly proximal end, said first segment movable with respect to said handle assembly, said first segment having a tip and a first blade depending from said tip,
        (iii) a second segment extending from said handle assembly proximal end, said second segment movable with respect to said handle assembly, said second segment having a tip and a second blade depending from said tip,
        (iv) each of said first and second blades having a leading edge and a trailing edge, said handle assembly movable for: (i) moving said first and second blades into contact with one another; and (ii) for moving said first and second blades apart from one another; and said trailing edges forming a single exposed and unenclosed cutting edge when said first and second blades are moved into contact one with one another;
    (b) gripping said instrument to bring said blades into contact to form a single exposed and unenclosed edge;
    (c) drawing said cutting edge across said nucleus to make a first incision;
    (d) placing said first and second blades within said incision; and (e) gripping said instrument to move said blades apart from one another whereby said incision is widened to split said nucleus.

10. The method of claim 9 further comprising the steps of:
(f) drawing said cutting edge across said nucleus to deepen said incision; and
(g) repeating steps (d) and (e).

* * * * *